United States Patent
Zamani et al.

(10) Patent No.: US 12,064,865 B2
(45) Date of Patent: Aug. 20, 2024

(54) PROXIMITY SENSING AUTONOMOUS ROBOTIC SYSTEMS AND APPARATUS

(71) Applicant: Cobionix Corporation, Kitchener (CA)

(72) Inventors: Nima Zamani, Kitchener (CA); Timothy Lasswell, Kitchener (CA)

(73) Assignee: Cobionix Corporation, Kitchener (CA)

( * ) Notice: Subject to any disclaimer, the term of this patent is extended or adjusted under 35 U.S.C. 154(b) by 276 days.

(21) Appl. No.: 17/746,910

(22) Filed: May 17, 2022

(65) Prior Publication Data

US 2022/0362944 A1 Nov. 17, 2022

Related U.S. Application Data

(60) Provisional application No. 63/189,642, filed on May 17, 2021.

(51) Int. Cl.
*B25J 13/00* (2006.01)
*B25J 9/00* (2006.01)
(Continued)

(52) U.S. Cl.
CPC ........... *B25J 13/086* (2013.01); *B25J 9/0009* (2013.01); *B25J 9/042* (2013.01); *B25J 9/1666* (2013.01);
(Continued)

(58) Field of Classification Search
CPC ........ B25J 13/086; B25J 9/0009; B25J 9/042; B25J 9/1666; B25J 9/1689; B25J 11/009; B25J 13/089; B25J 19/023
See application file for complete search history.

(56) References Cited

U.S. PATENT DOCUMENTS

| 4,996,753 A | 3/1991 | Jones |
| 9,645,019 B2 | 5/2017 | Duchaine et al. |
(Continued)

FOREIGN PATENT DOCUMENTS

| DE | 102019105820 A1 | 9/2020 |
| DE | 102019125117 B4 | 12/2020 |
(Continued)

OTHER PUBLICATIONS

Intenational Search Report from corresponding PCT application No. PCT/CA2022/050778, dated Aug. 25, 2022.

*Primary Examiner* — Kira Nguyen
(74) *Attorney, Agent, or Firm* — James W. Hinton; Kent C. Howe; Daniel Biggs

(57) ABSTRACT

A proximity sensing autonomous robotic system and apparatus is provided. The robot includes one or more vision modules for viewing the environment for depth perception, object detection, object avoidance and temperature detection of objects. A proximity sensing skin is laminated on one or more parts of the robot. The proximity sensing skin includes a plurality of proximity sensors and mechanical stress sensors for collision avoidance, speed control and deceleration of motion near detected objects, and touch recognition. The proximity sensing skin may include conductive pads for contacting different materials in a composite part to inhibit galvanic corrosion. The robot includes an end effector to which different tools may be attached for performing different tasks. The end effector includes a mounting interface with connections for supplying power and hydraulic/pneumatic control of the tool. All wiring to the sensors and vision modules are routed internally within the robot.

20 Claims, 12 Drawing Sheets

(51) Int. Cl.
*B25J 9/04* (2006.01)
*B25J 9/16* (2006.01)
*B25J 11/00* (2006.01)
*B25J 13/08* (2006.01)
*B25J 19/02* (2006.01)

(52) U.S. Cl.
CPC ........... *B25J 9/1689* (2013.01); *B25J 11/009* (2013.01); *B25J 13/089* (2013.01); *B25J 19/023* (2013.01)

(56) References Cited

U.S. PATENT DOCUMENTS

| | | |
|---|---|---|
| 10,576,644 B2 | 3/2020 | Fauteux et al. |
| 11,007,636 B2 | 5/2021 | L'Ecuyer et al. |
| 2016/0158942 A1* | 6/2016 | Augenbraun ........ B25J 11/0085 901/10 |
| 2018/0264648 A1 | 9/2018 | Kim et al. |
| 2019/0143522 A1* | 5/2019 | Miyazawa ............. B25J 9/1676 700/258 |
| 2019/0193267 A1* | 6/2019 | Peng ...................... B25J 19/06 |
| 2019/0240835 A1 | 8/2019 | Sorin et al. |
| 2020/0086479 A1 | 3/2020 | Messier et al. |
| 2020/0086504 A1 | 3/2020 | L'Ecuyer et al. |
| 2020/0086507 A1 | 3/2020 | Fortin |
| 2020/0180162 A1* | 6/2020 | Roziere ................. B25J 19/066 |
| 2020/0230817 A1 | 7/2020 | Han |
| 2020/0306979 A1 | 10/2020 | Paulson et al. |
| 2020/0361080 A1 | 11/2020 | Bergeron et al. |
| 2020/0361096 A1 | 11/2020 | Duhamel et al. |
| 2020/0368920 A1* | 11/2020 | Thunell ............... B25J 15/0408 |
| 2020/0377085 A1 | 12/2020 | Floyd-Jones et al. |
| 2020/0398428 A1 | 12/2020 | Murray et al. |
| 2021/0001484 A1 | 1/2021 | Bogart et al. |
| 2021/0016447 A1* | 1/2021 | Iwayama ............... B25J 13/086 |
| 2021/0023706 A1 | 1/2021 | Sorin et al. |
| 2021/0053220 A1 | 2/2021 | Ames |
| 2021/0069898 A1 | 3/2021 | Duan et al. |
| 2021/0069903 A1 | 3/2021 | Duan et al. |
| 2021/0069904 A1 | 3/2021 | Duan et al. |
| 2021/0069908 A1 | 3/2021 | Rohaninejad et al. |
| 2021/0146542 A1* | 5/2021 | Kiyosawa ............. B25J 13/089 |
| 2021/0178591 A1 | 6/2021 | Floyd-Jones et al. |
| 2021/0197366 A1 | 7/2021 | Lavigne et al. |
| 2021/0197400 A1 | 7/2021 | Messier et al. |
| 2021/0220994 A1 | 7/2021 | Colasanto et al. |
| 2021/0229292 A1 | 7/2021 | Liu et al. |
| 2021/0233246 A1 | 7/2021 | Liu et al. |
| 2021/0233258 A1 | 7/2021 | Sieb et al. |
| 2021/0276185 A1 | 9/2021 | Shentu et al. |
| 2021/0276187 A1 | 9/2021 | Tang et al. |
| 2021/0276188 A1 | 9/2021 | Tang et al. |

FOREIGN PATENT DOCUMENTS

| | | |
|---|---|---|
| DE | 202020106712 U1 | 12/2020 |
| DE | 202020106713 U1 | 12/2020 |
| DE | 202020106716 U1 | 12/2020 |
| DE | 202020106717 U1 | 12/2020 |
| DE | 202020106718 U1 | 12/2020 |
| DE | 202020106711 U1 | 1/2021 |
| DE | 202019107044 U1 | 3/2021 |
| DE | 202019005591 U1 | 4/2021 |
| DE | 102019134392 A1 | 6/2021 |
| DE | 102019134794 B4 | 6/2021 |
| DE | 102020102576 A1 | 8/2021 |
| DE | 102019135732 B4 | 9/2021 |
| EP | 3354418 A2 | 8/2018 |
| EP | 3579100 A1 | 12/2019 |
| EP | 3866113 A1 | 8/2021 |

* cited by examiner

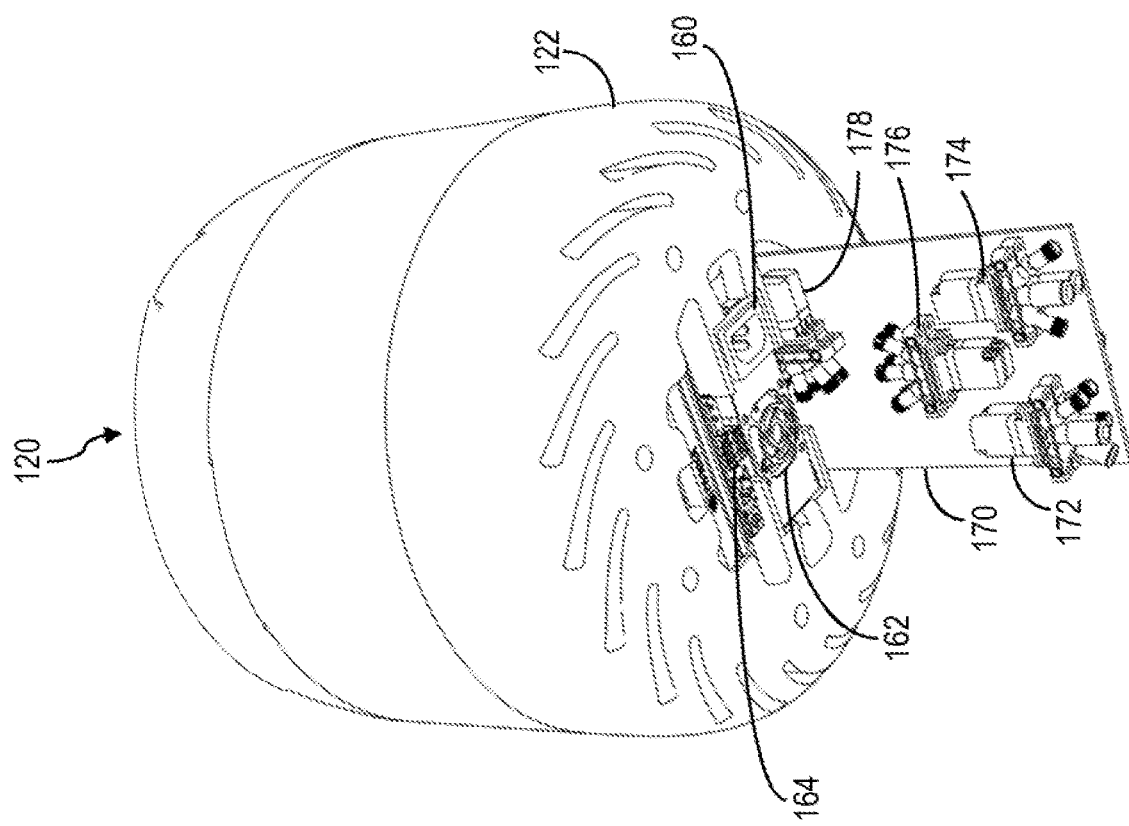

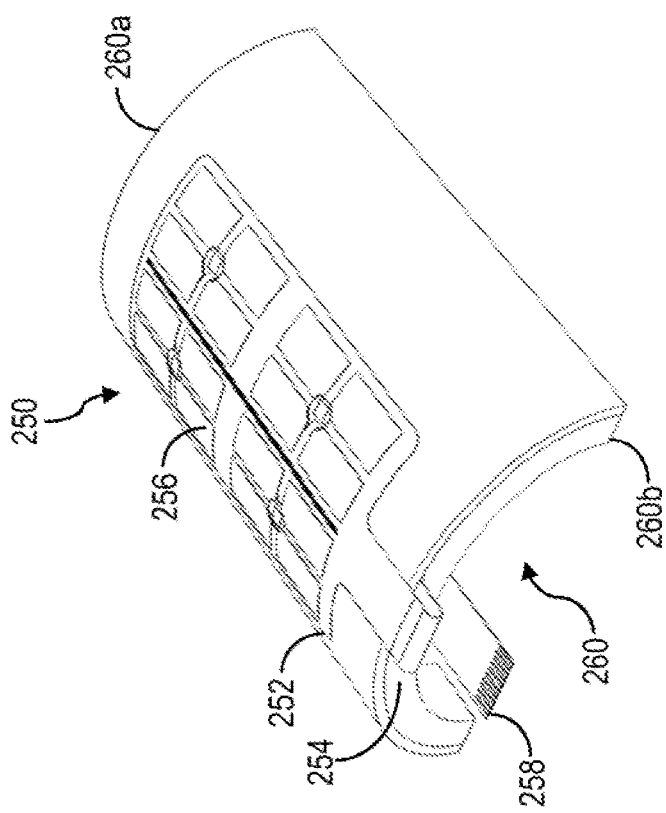
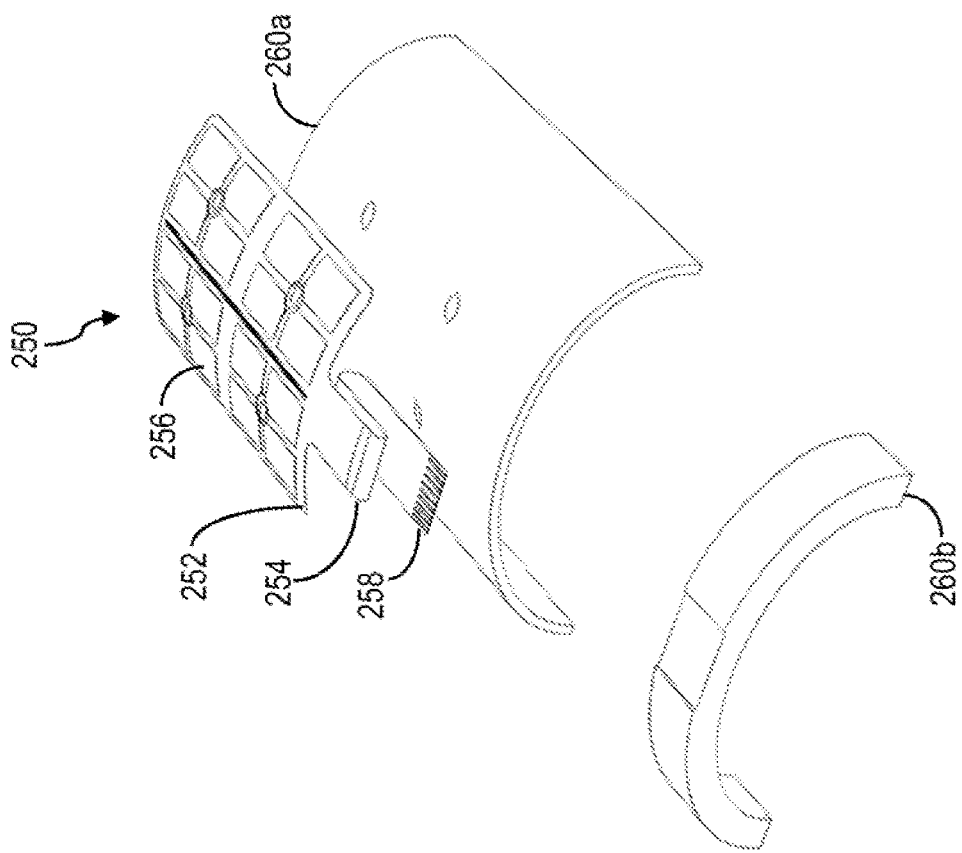
FIG. 6B
FIG. 6A

PROXIMITY SENSING AUTONOMOUS ROBOTIC SYSTEMS AND APPARATUS

TECHNICAL FIELD

The embodiments disclosed here related to autonomous robotics, and, in particular to a proximity sensing autonomous robotic system and apparatus for performing tasks in variable environments.

INTRODUCTION

An autonomous robot is a type of robot that performs behaviors and tasks with a high degree of autonomy (without external influence). In contrast to automated robots, which perform the same sequence of tasks in a highly controlled environment to complete the end goal, autonomous robots are able to modify the sequence and specifics of tasks to overcome unpredictable variables in more chaotic environments and complete the end goal.

Autonomous robots are typically specialized and trained to perform a specific task. As such, autonomous robots cannot easily be adapted or modified to perform other tasks without significant modification. A further difficulty in implementing autonomous robots is that autonomous robots are typically not manufactured to be used "out of the box." Rather, sensors and cameras for autonomous operation are added or retrofitted onto the robot. Integrating the sensors and cameras can be difficult, or impractical. Furthermore, integration of sensors typically involves routing wires or cabling along the exterior of the robot which can limit installation location and operation of the robot, particularly if the robot is operating in close proximity to other robots or objects, which may become snagged on the wiring.

Modern robots often use composite parts. While lightweight, composite parts can suffer from galvanic corrosion caused by different conductive materials with different electrical conductivities being in direct contact. This problem is exasperated in humid and damp environmental conditions. Anti-corrosion sprays or coatings can be applied to composite parts to inhibit galvanic corrosion, however the effectiveness of such coatings decreases with time. Furthermore, it may not be possible to coat the interior of composite parts which would require disassembly of the robot.

Accordingly, there is a need for new autonomous robotic systems and apparatus that have built-in proximity sensing and corrosion inhibition for easy installation and autonomous operation.

SUMMARY

The autonomous robot disclosed in this patent application represents a platform technology that allows several design embodiments to be created for specific applications, some of which are further discussed in the present application. Several design embodiments of the autonomous robot platform itself are also disclosed.

The autonomous robot solution for each end-use application discussed consists of two components. The first component is the autonomous robotic platform which acts as the brains and body of the robot. The second component is the end effector which acts as the hand of the robot. This two-component approach allows the autonomous robotics platform to be trained on a multitude of procedural tasks and readily deployed in new applications by just changing the end effector which is specific to each application. While some end effectors will be tailored to specific tasks, others will be broader, such as a fully dexterous robotic hand, further increasing the scope of environments in which these autonomous robots can operate.

According to an embodiment there is a proximity sensing skin. The proximity sensing skin comprises a flexible conductive material for laminating to a surface, the conductive material having a plurality of sensors arranged thereon. The plurality of sensors include: at least one capacitive sensor, for sensing the proximity of objects up to ~10 centimeters from the surface; a single point time of flight sensor, for sensing the proximity of objects from ~10 centimeters up to ~2 meters from the surface; and a copper trace for measuring mechanical strain/stress force on the surface to which the proximity sensing skin is laminated. The flexible conductive material relays signals from the plurality of sensors to a servo controller configured to move the surface in response to the signals from the plurality of sensors.

According to another embodiment, there is an autonomous robot apparatus. The autonomous robot apparatus includes an articulated robotic arm having a plurality of limb segments connected by hollow joints. The limb segments are rotatable about the joints to move the robotic arm in three dimensions.

The robot apparatus includes an end effector removably attached to a terminal limb segment. The end effector comprises a mounting interface for removably attaching a tool. The mounting interface comprising a latch mechanism for locking the tool to the mounting interface; a first vision module for measuring the attachment or detachment of the tool at the mounting interface.

The robot apparatus further includes a base attached to the robotic arm. The base comprises a second vision module for detecting objects in proximity to the robotic apparatus. The second vision module comprises a pair of RGB cameras for stereoscopic depth perception of objects in an environment around the robot apparatus; a far-infrared thermal camera for measuring temperature of the objects; and a single point time of flight (ToF) depth sensor for measuring distances to the objects. The base further includes a three-axis gimbal configured to point the second vision module to capture a 360-degree view of the environment around the robot apparatus. The robot apparatus is configured to autonomously articulate the robotic arm to perform one or more trained tasks using the tool while avoiding collisions with the objects detected by the second vision system.

According to another embodiment, there is an autonomous robotic system using the autonomous robot apparatus for administering injection. The system comprises a support structure for mounting the base of the autonomous robot apparatus The support structure comprises a first receptacle for storing disposable cartridges filled with a fluid to be injected into a patient, at least a second receptacle for storing waste, and a reloading mechanism for loading a disposable cartridge into a tip of the tool attached to the end effector of the robot apparatus.

The autonomous robot apparatus is configured to move the tool adjacent to the reloading mechanism when the tip is unloaded and move the tool above the second receptacle to dispose of the disposable cartridge after injection while avoiding collisions with the objects detected by the second vision system Other aspects and features will become apparent, to those ordinarily skilled in the art, upon review of the following description of some exemplary embodiments.

BRIEF DESCRIPTION OF THE DRAWINGS

The drawings included herewith are for illustrating various examples of articles, methods, and apparatuses of the present specification. In the drawings:

FIG. 2E is a bottom view of the bottom of the base shown in FIGS. 1A and 1B;

FIGS. 6A-6B are an exploded and a perspective view, respectively, of a corrosion inhibiting proximity sensing skin applied to a robot composite part, according to an embodiment;

DETAILED DESCRIPTION

Figure 1B:
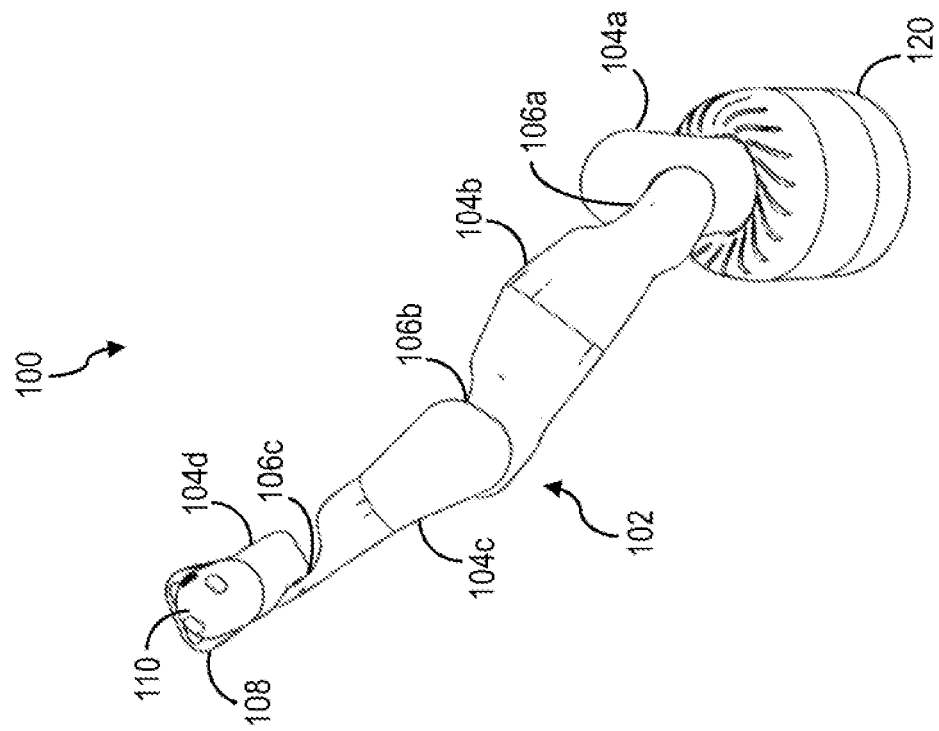
FIGS. 1A-1B are perspective views of an autonomous robot apparatus, according to an embodiment.

Various apparatuses or methods will be described below to provide an example of each claimed embodiment. No embodiment described below limits any claimed embodiment and any claimed embodiment may cover processes or apparatuses that differ from those described below. The claimed embodiments are not limited to apparatuses or processes having all of the features of any one apparatus or process described below or to features common to multiple or all of the apparatuses described below.

One or more systems described herein may be implemented in computer programs executing on programmable computers, each comprising at least one processor, a data storage system (including volatile and non-volatile memory and/or storage elements), at least one input device, and at least one output device. For example, and without limitation, the programmable computer may be a programmable logic unit, a mainframe computer, server, and personal computer, cloud based program or system, laptop, personal data assistance, cellular telephone, smartphone, or tablet device.

Each program is preferably implemented in a high level procedural or object oriented programming and/or scripting language to communicate with a computer system. However, the programs can be implemented in assembly or machine language, if desired. In any case, the language may be a compiled or interpreted language. Each such computer program is preferably stored on a storage media or a device readable by a general or special purpose programmable computer for configuring and operating the computer when the storage media or device is read by the computer to perform the procedures described herein.

A description of an embodiment with several components in communication with each other does not imply that all such components are required. On the contrary a variety of optional components are described to illustrate the wide variety of possible embodiments of the present invention.

Further, although process steps, method steps, algorithms or the like may be described (in the disclosure and/or in the claims) in a sequential order, such processes, methods and algorithms may be configured to work in alternate orders. In other words, any sequence or order of steps that may be described does not necessarily indicate a requirement that the steps be performed in that order. The steps of processes described herein may be performed in any order that is practical. Further, some steps may be performed simultaneously.

When a single device or article is described herein, it will be readily apparent that more than one device/article (whether or not they cooperate) may be used in place of a single device/article. Similarly, where more than one device or article is described herein (whether or not they cooperate), it will be readily apparent that a single device/article may be used in place of the more than one device or article.

The robotic system and apparatus described herein include a plurality of fixed and movable sensors for assessing the local environment to perform autonomous actions. The sensors are wholly incorporated into the robotic system and apparatus such that they are meant to be used out of the box, as a cohesive self-contained unit, in conjunction with dedicated artificial intelligence (AI) and software. Additional sensors may be incorporated for application-specific needs. The AI and software are fully integrated to the robotic system and apparatus for plug-and-play implementation into larger systems without requiring configuration apart from an initial setup when the robot apparatus is first installed.

When a tilde (~) is used herein, it signifies a range of ±10% of the indicated value. For example, ~1.0 means between 0.9 to 1.1.

Figure 1A:
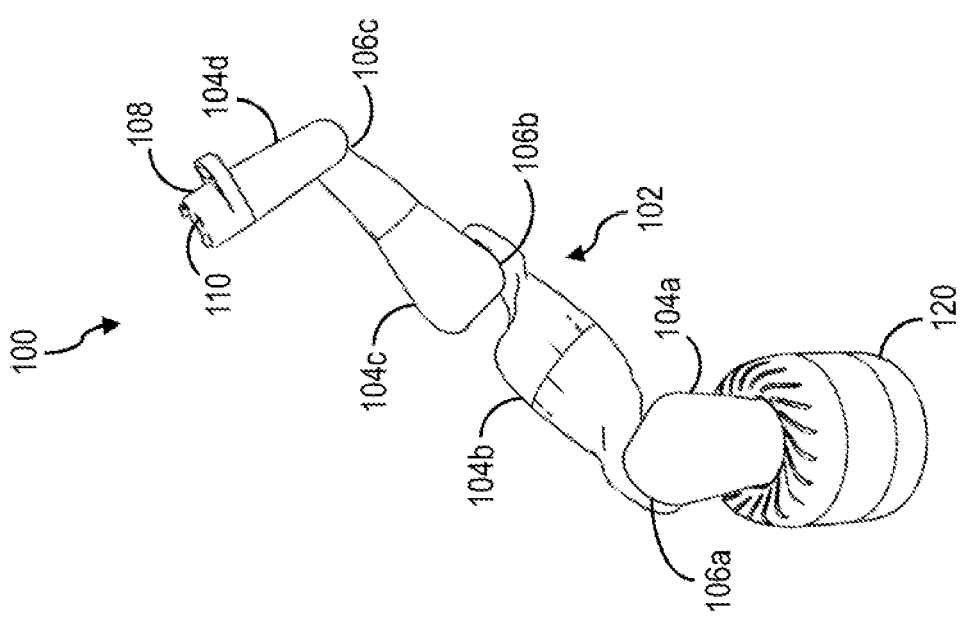

Referring to FIGS. 1A and 1B, shown therein are perspective views of an autonomous robot apparatus 100, according to an embodiment. The robot 100 includes an articulated arm 102. The arm 102 includes limb segments 104a, 104b, 104c, 104d connected at joints 106a, 106b, 106c. The limb segments 104b, 104c, 104d are rotatable about the joints 106a, 106b, 106c. The limb segment 104a is rotatable about a base 120. The connectivity of the limb segments 104a, 104b, 104c, 104d via the joints 106a, 106b, 106c provides for the robot 100 to articulate the arm 102 in three dimensions.

Each limb segment 104a, 104b, 104c, 104d is preferably fabricated using primarily carbon fiber composite material to be relatively light weight and resilient. According to other embodiments the limb segments 104a, 104b, 104c, 104d may be constructed of other composite materials such as fiberglass.

Each limb segment 104a, 104b, 104c, 104d houses one or more servo motors for actuating the limb segment. The servo motors are configured to implement a current feedback mechanism for sensing mechanical resistance experienced by the servo when moving a limb segment or joint. By measuring the forces/torque on each joint/servo, by the current feedback mechanism, the mechanical resistance can be measured.

All wiring to the servo motors is routed through the interior of the limb segments 104a, 104b, 104c, 104d and through the hollow joints 106a, 106b, 106c, with no wiring or cables present on the exterior of the robot 100 which can limit installation and movement of the robot 100 during operation The robot 100 includes an end effector 108 for removably attaching tools (not shown) at a mounting interface 110. The end effector 108 is described in more detail with reference to FIG. 3.

The robot 100 includes a base 120. The base 120 is fixed to a support structure (not shown) for supporting the arm 102. Generally, the base 120 includes components for control of the robot 100. The base 120 is described in more detail with reference to FIGS. 2A-2E.

The robot 100 includes computational power as well as sensors for autonomous applications. The sensors include external sensors including vision systems such as LIDAR, time of flight (TOF), and stereoscopic depth sensors. Some of the sensors are stationary at the base 120 of the robot 100 to sense and generate information regarding the environment the robot 100 is operating in. According to an embodiment, the base 120 includes a rotating lidar system or multiple stationary depth sensors located at specific separation angles. Other sensors are mounted to the arm 102 of the robot 100 as well as the end effector 108 for operation-specific tasks. These sensors include a proximity sensing skin as well as vision/depth sensors as described below.

The sensors are wholly incorporated into the robot 100 and are meant to be used out of the box as a cohesive unit in conjunction with dedicated software. Additional sensors can be incorporated into the tool 112 for application-specific needs. The robot 100 also comes with AI and autonomous software fully integrated and ready to use. The overall software workflow is described in detail below.

Referring to FIGS. 2A-2D, shown therein are various views of the base 120 shown in FIGS. 1A and 1B. The base 120 includes a bottom 122 for securing the base 120 to a support structure. The bottom 122 includes openings 124 through which fasteners are passed to secure the base 120 to the support structure. The bottom 122 includes a plurality of vent holes 132 to allow for air to circulate through the bottom 122 to cool the power supply unit.

The base 120 includes a top 126. The top 126 houses a disc-shaped printed circuit board (PCB) including the electrical components for controlling the robot and processing the signals received from the proximity sensors on the robot. The PCB includes at least one processor and a memory for storing processor-executable instructions, including software and AI algorithms/models. The instructions, when executed by the processor, configure the robot to autonomously perform a plurality of trained tasks or behaviors and/or process the signals from the sensors to autonomously control the robot during performance of the trained tasks in variable environments.

When it comes to collaborative or autonomous robotics, especially when dealing in everyday world settings, managing randomness and chaos becomes crucial. This randomness is mitigated by incorporating a sim-to-real simulation feedback loop workflow into the robot's operating instructions. In this workflow, the simulations predict all the variations and randomness of the world through the process of domain randomization. The simulations could be task or domain-specific. The synthetic data generated by the simulations are subsequently used to train a series of artificial intelligence models to be able to predict and inference in real-world settings. Additionally, the AI models can be continuously improved while being used in the real world using methods such as transfer learning.

The robot is an IoT device that runs AI on the Edge. The software of the robot is able to be updated over-the-air via a Wi-Fi or 5G network without any interruption while being used in the field. The top 126 houses wireless communication components for connecting to a WiFi or 5G network.

The top 126 further houses a speaker and indicator LEDs for communicating the operational status of the robot to a user. For example, a green LED indicates when the robot is operating normally; a red LED or an audible alarm indicates an error.

The top 126 further houses a microphone for receiving commands from the user to control operation of the robot. One of the main aspects of this embodiment of the robot is the use of Vocal Programming Language (VPL). The intention of the programming language is to use automatic speech recognition (ASR) and natural language processing (NLP) techniques in order to define AI-powered procedural tasks for the robot without having to manually program anything. This will make the robot significantly more useful for any client to use and will lead to significant adoption of the robots in everyday life.

The top 126 includes a plurality of vent holes 128 to allow for air to circulate through the top 126 to cool the components therein. The vent holes 128 further allow for audio from the speaker, and sound to the microphone, to pass through. Light from the indicator LEDs is also visible through the vent holes 128.

The base 120 includes a middle 130 that is recessed relative to the top 126 and the bottom 122. The middle 130 houses a vision module 140 (for ease of illustration, the vision module 140 is omitted in FIGS. 2C and 2D).

Figure 2B:
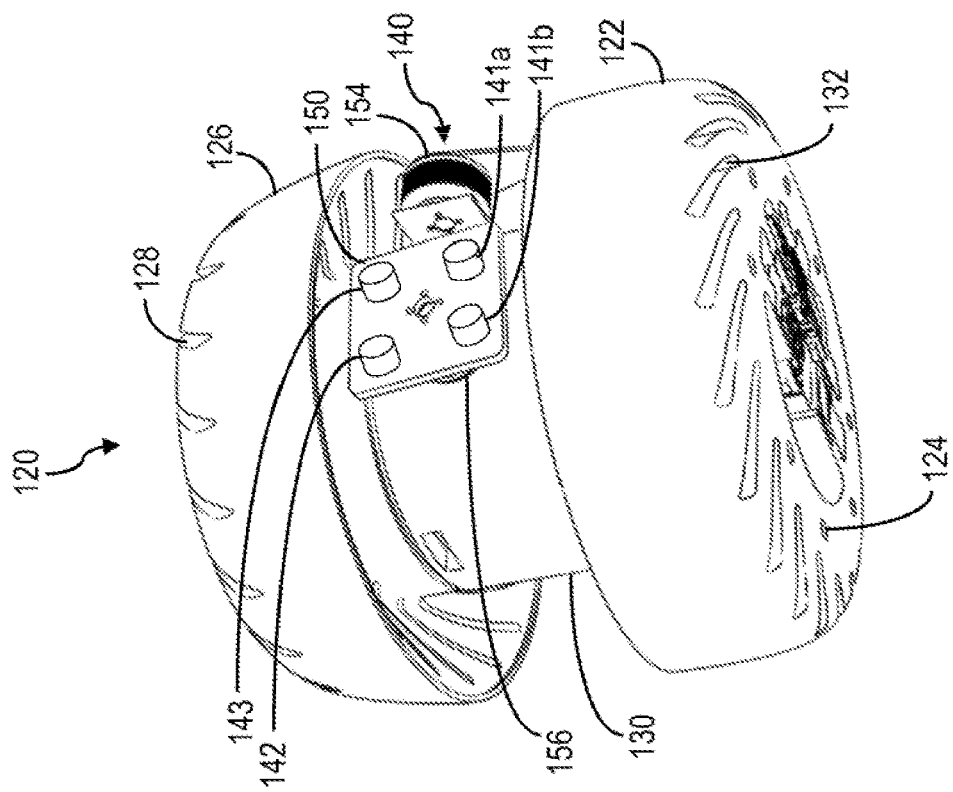
FIGS. 2A-2B are a side and a perspective view, respectively, of the base shown in FIGS. 1A and 1B.
Figure 2A:
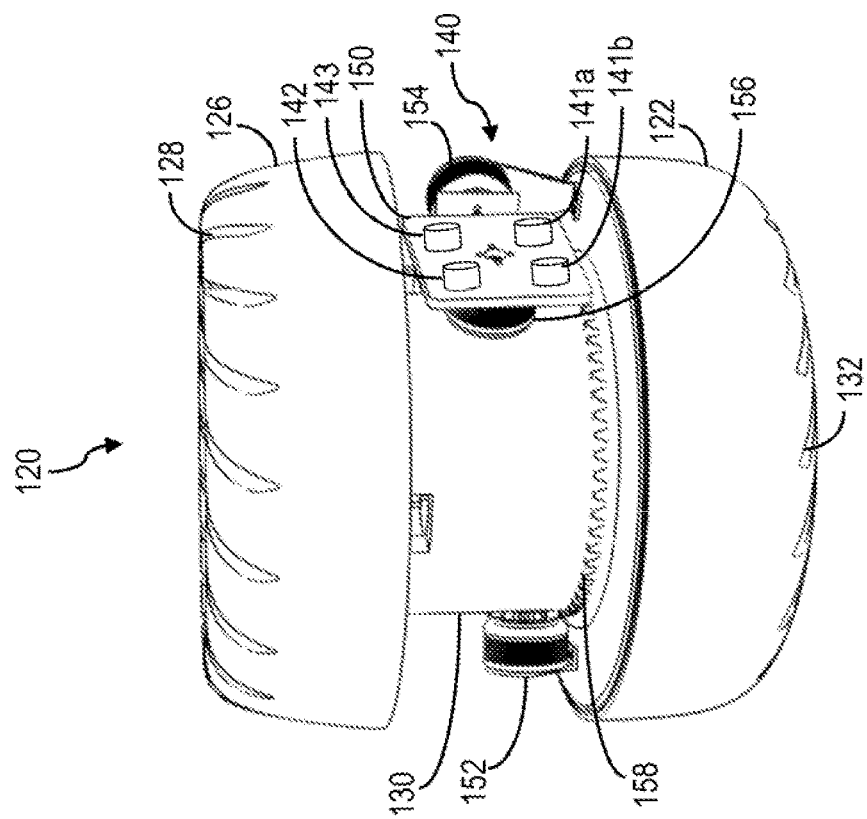

Now referring to FIGS. 2A-2B, the vision module 140 is a critical part of the autonomous robot. The vision module 140 consists of a plurality of camera sensors 141a, 141b, 142, 143 to accomplish different tasks including depth perception, object detection, object avoidance and temperature detection of objects. The vision module 140 includes two RGB cameras 141a, 141b using global illumination, a ToF (time of flight) depth sensor 142, and an FIR (far-infrared) thermal camera 143. For the purposes of transferring the signals to the base of the robot through the hollow shaft of the joints, all the signals from the vision module 140 are carried by a single USB cable. Signals from the camera sensors 141a, 141b, 142, 143 are first converted from MIPI or I2C interface to USB using a dedicated integrated circuit. Subsequently the converted signals are combined into a single USB cable by a USB-Hub type integrated circuit.

The purpose of having two RGB cameras 141a, 141b is to provide stereoscopic depth perception for VR/AR applications and for calibration of the thermal camera 143. The emissivity calibration of the thermal camera 143 can be calculated and adjusted in real time, based on AI-based object detection via the ToF sensor 142, and the RGB cameras 141a, 141b. Using the corresponding emissivity of the detected object, its temperature can be estimated with higher accuracy.

According to various embodiments, the vision module 140 may be used in both the end effector (i.e., end effector 108 in FIGS. 1A-1B) and/or the base 120 of the robot. In the embodiment shown, the vision module 140 is mounted on a three-axis gimbal 150 on the base 120 of the robot to give a 360-degree view of the environment around the robot.

The orientation of the gimbal 150 is controlled by three servo motors 152, 154, 156 to point the vision module 140 in the appropriate direction. The servo motors 152, 154, 156 may be linear or rotary actuators. A first servo 152 controls the 360-degree translocation of the gimbal 150 around the circumference of the middle 130 of the base 122 to point the vision module 140 in a general direction. The first servo 152 moves the gimbal 150 along a track 158 running around the circumference of the middle section 130 adjacent to the bottom 122. The second servo 154 is used for fine control of the vertical tilt of the gimbal 150. The third servo 156 is used for fine control of the horizontal tilt of the gimbal 150.

Additionally, the gimbal 150 can be used for real-time orientation for VR/AR application of telerobotics. For example, an operator of the robot could connect to the robot, wired or wirelessly, using a VR/AR headset and the 3D orientation of the headset is transferred to the gimbal 150 to point the vision module 140 in real-time. The VR/AR headset may then display the views or measurements of the camera sensors 141a, 141b, 142 143 to the user in real time.

In other embodiments, multiple vision modules 140 are statically positioned and oriented on the base 120. The 360-degree environment perception is constructed using software by stitching the images from the different vision modules 140.

Figure 2D:
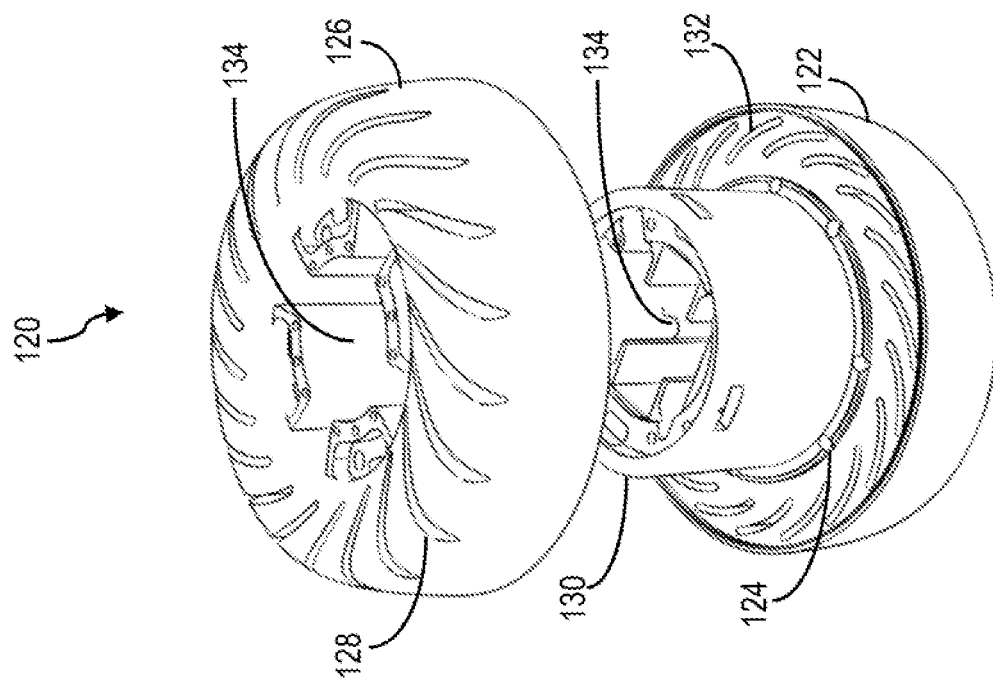
FIGS. 2C-2D are top and bottom exploded views, respectively, of the base shown in FIGS. 2A and 2B.
Figure 2C:
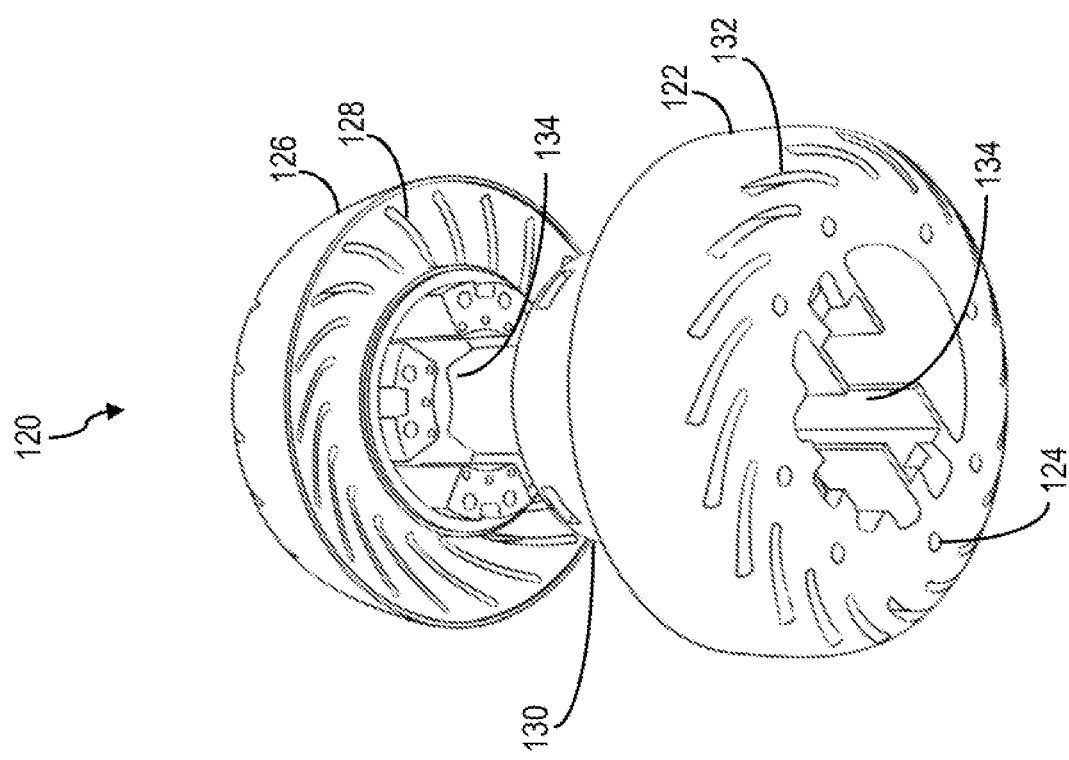

Now referring to FIGS. 2C-2D, the base 120 includes a central hollow 134 that passes through the top 126, the middle 130 and the bottom 122 of the base 120. Advantageously, the central hollow 134 allows for electrical wiring of components of the base 120, and hydraulic/pneumatic lines to the end effector, to be routed through the central hollow 134 rather than being routed on the exterior of the robot which can limit installation and movement of the robot during operation. This enables relatively easy plug-and-play installation of the robot since all cabling required for power supply to the robot, hydraulic/pneumatic fluid supply to the end effector, etc. is routed through the central hollow 134.

Referring to FIG. 2E, shown therein is a bottom view of the base 120. The bottom 122 of the base 120 houses a power supply unit 160 for connecting to a power source to provide electrical power to the robot. The bottom 112 further houses a fan 162 to circulate air through the bottom 122 of the base 120 to cool the components therein. The bottom 112 also includes I/O connectors 164 for connecting a device to configure and set up the robot for operation. For example, a VR/AR head mounted display can be connected to the robot via the IO connectors 164, for a user to observe the field of view captured by the vision module 140 to calibrate sensor view angles and sighting distances. The I/O connectors 164 are also used to connect the robot to peripheral equipment such as a display, an external sensor, or other device for integration with the robot. The I/O connectors 164 include, at least, USB ports.

The bottom 112 of the base 120 further houses a valve array 170. For ease of illustration, the valve array 170 is shown partially removed from the bottom 122. The valve array 170 includes a plurality of solenoid valves 172, 174, 176, 178, in fluidic connection, for regulating fluid supply to two lines going to the end effector of the robot. The valve array 170 is configured to fluidically connect 5 or 6 input fluids (either a liquid or a gas) to the two output lines going to the end effector. The input fluids include hydraulic/pneumatic fluid for hydraulic/pneumatic control of a tool attached to the end effector. The inputs fluids include fluids for use by the tool for performing various tasks, for example, distilled/deionized water, sanitization liquids such as IPA, soap, or other chemicals, filtered clean air, compressed air, and pure compressed gases (nitrogen, oxygen, argon, etc.).

The output lines going to the end effector 108 are interchangeable at any time via the valve array 170. This allows for one of the lines to be washed, with IPA or soap, then rinsed with water, then dried with air, while the other line supplies working fluid to the end effector 108.

Figure 3B:
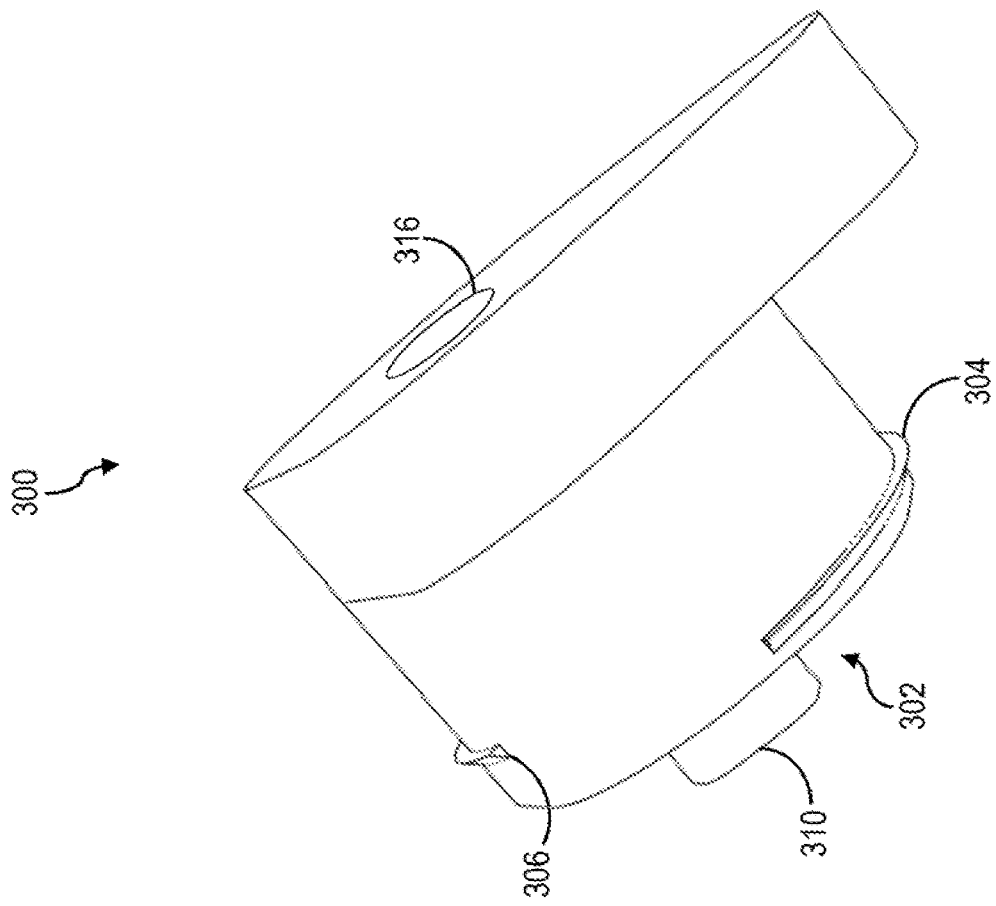
FIGS. 3A-3B are a front and a side perspective view, respectively, of an end effector, according to an embodiment.
Figure 3A:
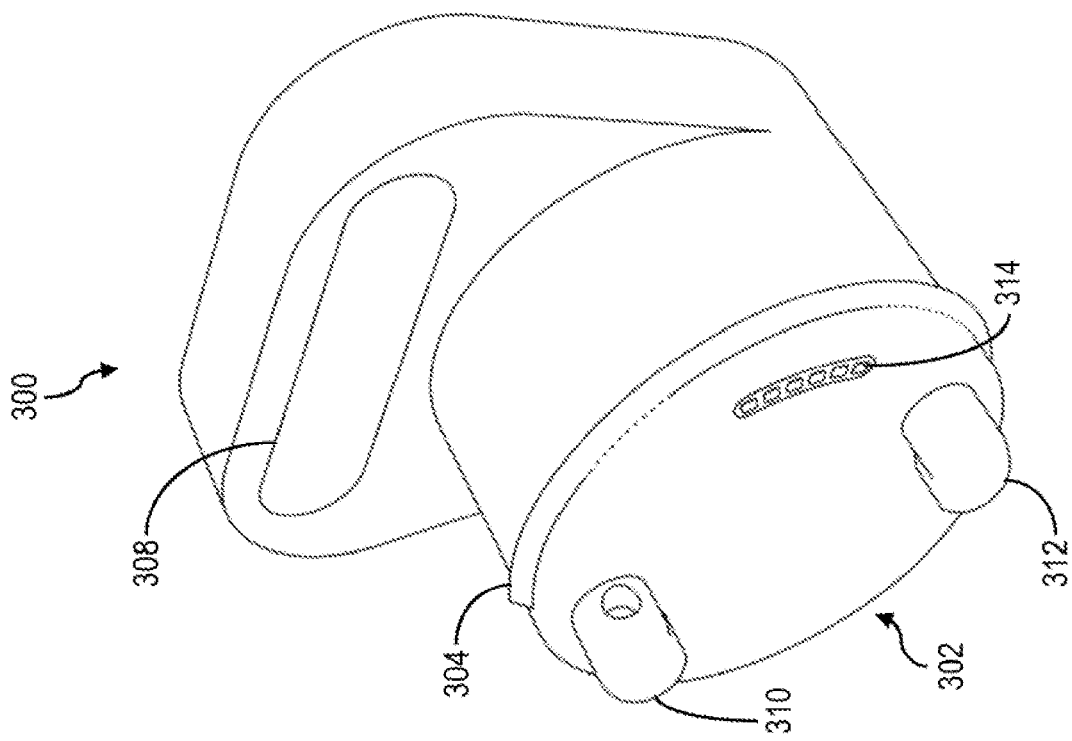

Referring to FIGS. 3A-3B, shown therein is an end effector 300, according to an embodiment. The end effector 300 may be the end effector 108 in FIGS. 1A-1B. The end effector 300 may be specifically adapted to mount a particular tool to the robot. The end effector 300 is detachable from the robot to accommodate different tools for different tasks. The end effector 300 includes a mounting interface 302 for attaching to the tool. The mounting interface 302 includes a mechanical latch-based or magnetic-based mounting mechanism. Latched-based mechanisms include rotary or translational mechanisms as described below.

In the embodiment shown, the mounting interface 302 includes a rotary mechanical latch-based mechanism similar to DSLR cameras' detachable lenses. The mounting interface 302 includes a helical collar 304 for engaging a helical groove on the tool. The end effector 300 is rotatably mated to the tool whereby rotation of the end effector 300 relative to the stationary tool causes the helical collar 304 to screw into and engage the helical groove in the tool. Unlike DSLR cameras where the rotary motion is provided by the human user, the rotary motion is provided by a last Degree of Freedom (DOF) servo in the end effector 300, in this embodiment. This will significantly reduce the complexity and the need for additional actuation and motion units for attachment of the tool.

The robotic arm (i.e., robotic arm 102 in FIGS. 1A-1B) positions the end effector 300 adjacent to a stationary-held tool and starts the rotary motion leading to the tool being screwed onto the end effector 304 at the mounting interface 302; this motion finishes when the rotation reaches the end of a helical collar 304 and the tool hits a hard stop 306 of the end effector 300. At this point, the rotational torque of the last DOF servo in the end effector 300 will significantly increase which lets the robot know the tool is fully mounted to the end effector 300, and the latch is locked by mechanical or electrical means to lock the tool in place.

According to other embodiments, the mounting interface 302 includes a translational mechanical latch-based mounting mechanism. The translational mechanical latch-based mechanism works by the robotic arm moving the end effector 300 in a linear motion onto the stationary-held tool until reaching the hard stop and activating a latch in the process which locks the tool to the end effector 300 at the mounting interface 302. The linear motion ends with the increase in mechanical resistance to all the DOFs servos of the robot.

Additionally, in both of the aforementioned mounting mechanisms (rotary or translational), sensors can be used to detect both the presence of the tool on the end effector 300 and/or the completion of the attaching/detaching processes. The end effector 300 includes a vision module 308. The vision module 308 is substantially similar to the vision module 104 described above and includes cameras and proximity sensors for detecting the tool and the attachment/detachment of the tool to the end effector 300.

Regardless of the mechanism of attachment (rotary or translational), the tool can be passive or active. Active tools are controlled and powered by the robot directly and automatically. The mounting interface 304 includes pneumatic/hydraulic connections 310, 312 and automatic release valves connected to two fluid supply lines for hydraulic/pneumatic control of the tool, if needed. The pneumatic/hydraulic connections 301, 312 on the mounting interface 304 align and connect to corresponding connectors on the tool when the tool is attached to the end effector 300. The pneumatic/ hydraulic connections 310, 312 and valves are connected to hydraulic/pneumatic fluid supply lines routed internally through an opening 316 in the end effector 300.

Control of the tool by the robot is via electrical connections 314. The electrical connections are formed by spring-loaded pogo pins and traces 314 on the mounting interface 302 which contact complementary pogo pins and traces on the tool when the tool is attached to the end effector 300. The electrical connections 314 include power lines, digital and communication lines (such as I2C, SPI, CAN, and USB), and high precision analog signal lines. The tool is hot-swappable, which provides the ability for the tool to be changed while the robot (and/or the tool) is powered and functioning. The location of the pogo pins 314 can either be on the front face of the mounting interface 302 (as shown) or on a side face of the mounting interface 302. According to embodiments wherein the electrical connections 314 are located on the side face of the mounting interface 302, there are leads extending from the tool to reach the electrical connections 314.

Figure 4B:
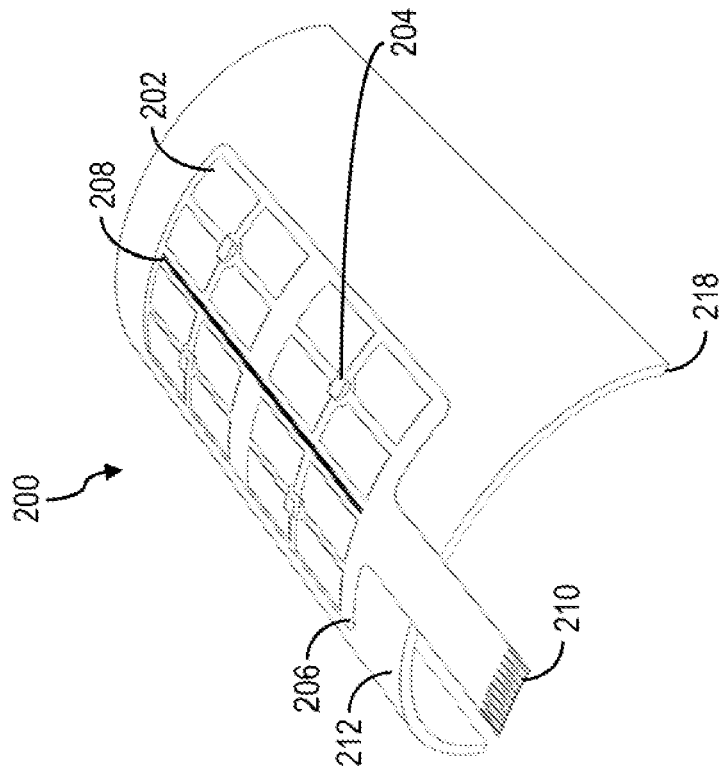
FIG. 4B is a perspective view of the proximity sensing skin of FIG. 4A applied to a robot surface, according to an embodiment.
Figure 4A:
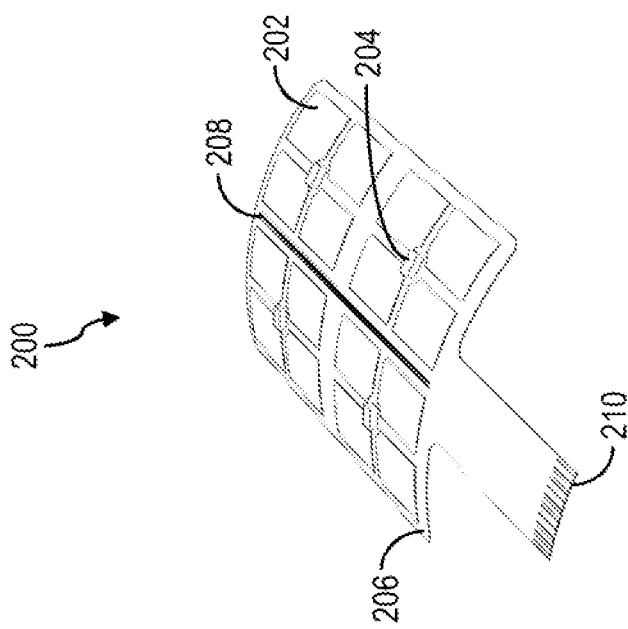
FIG. 4A is a perspective view of a proximity sensing skin, according to an embodiment.

Referring to FIG. 4A, shown therein is a proximity sensing skin 200, according to an embodiment. Generally, the proximity sensing skin 200 includes at least one capacitive sensor and one ToF sensor. According to various embodiments, the proximity sensing skin 200 may include several types of sensors including capacitive and resistive pressure sensors, light-based sensors such as infrared ToF and laser-based proximity sensors, and strain-gauge or strain-gauge-like stress sensors. The proximity sensing skin 200 is fabricated from flexible PCBs or flexible and stretchable conductive material/fabrics. Multiple types of sensors, as mentioned, could be incorporated into the proximity sensing skin 200 and subsequently use the data obtained by other sensors by using sensor fusion data processing techniques.

In the embodiment shown, the proximity sensing skin 200 comprises a plurality of copper capacitive sensors 202 and ToF (time of flight) sensors 204 arranged on a flexible PCB 206. The PCB 206 may be constructed from a capacitive film. The capacitive sensors 202 are arranged in sets of 4 capacitive sensors 202 in a 2×2 grid with a ToF sensor 204 in the center of each 2×2 grid. As shown, the proximity sensing skin 200 includes four 2×2 grids totaling 16 capacitive sensors 202 and 4 time of flight sensors 204. According to other embodiments, the arrangement of the capacitive sensors 202 and ToF sensors 206 on the PCB 206 may be varied for specific applications.

The capacitive sensors 202 are configured to detect the proximity of relatively close objects up to ~10 centimeters away from the sensor 202. The ToF sensors 204 are single point time of flight sensors comprising a phototransistor and an IR LED. The ToF sensors 204 are configured to detect the proximity of objects at longer distances of up to ~1 meter away from the sensor 204, but cannot detect objects at relatively short distances. Using the capacitive sensors 202 in combination with the ToF sensors 204 provides for a greater combined range of sensing of objects in very close proximity (within 10 cm) and objects at longer distances up to 1 meter.

The proximity sensing skin 200 includes a copper trace 208 for measuring mechanical strain on proximity sensing skin 200 and/or strain on a robotic surface the sensing skin 200 is applied to. The copper trace 208 shown in FIG. 4A appears linear, but actually zig-zags across the middle of the PCB 206 in a substantially linear path between the sensors 202, 204. If the sensing skin 200, or the robotic part to which it is applied experiences stresses, the copper trace 208 will in turn become stretched thus changing the resistance in the copper trace 208. The change in resistance of the copper trace 208 can be measured as an indication of the stress on the robotic part the sensing skin 200 is applied to.

The proximity sensing skin 200 includes circuits for supplying power to the sensors 202, 204, 208 and circuits for relaying signals from the sensors 202, 204, 208 to a controller on the robot via the connector 210.

Referring to FIG. 4B, shown therein is the proximity sensing skin 200 applied to a robot surface 212, according to an embodiment. The proximity sensing skin 200 is applied to the robot surface 212 to facilitate safe operation and collaboration between the robot and other robots, humans or objects in close proximity. The robot surface 212 could be anywhere on the robot including the base or the robotic arm; the proximity sensing skin 200 can also be applied to the detachable tools. In the embodiment shown, the robot surface 212 is on the exterior of the robot. According to other embodiments, the robot surface 212 to which the proximity sensing skin 200 is applied is an interior surface of the robot.

Figure 4C:
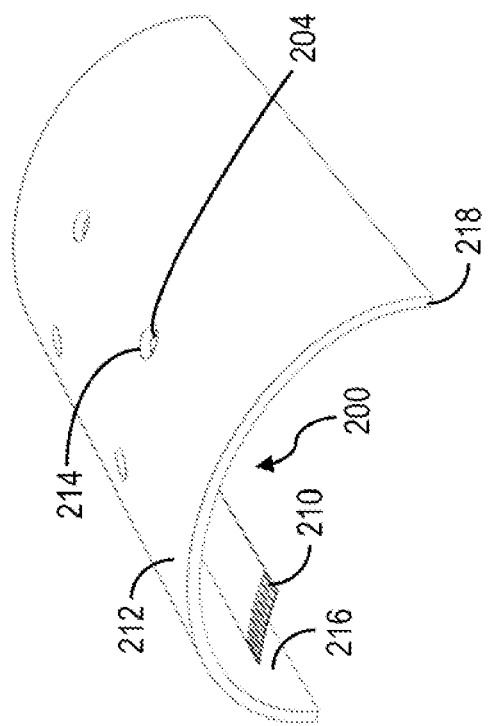
FIG. 4C is a perspective view of the proximity sensing skin of FIG. 4A, applied to a robot surface, according to another embodiment.

Referring to FIG. 4C, shown therein is the proximity sensing skin 200 applied to a robot surface 216, according to another embodiment. In this embodiment, the robot surface 216 to which the proximity sensing skin 200 is applied is on the interior of the robot. A robot part 218 that includes the robot surface 216 should be sufficiently thin and non-metallic to allow for the copper capacitive sensors 202 to sense the proximity of objects through the part 218.

The part 218 includes apertures 214 between the surfaces 212, 216. When the proximity sensing skin 200 is applied to the surface 216, the ToF sensor 204 is aligned with the aperture 214. The IR light emitted by ToF sensor 204, and reflections of the IR light from objects pass through the aperture 214 and are recorded by the ToF sensor 204.

Referring to FIGS. 4B-4C, the proximity sensing skin 200 may be incorporated into a monolithic part 218 of the robot's body itself. The proximity sensing skin 200 may be laminated to an exterior surface (FIG. 4B), or an interior surface (FIG. 4C) of the part 218 using epoxy resin to form a monolithic part 218. The PCB 206 can take any shape and match the curvature/contours of the carbon fibre composite part 218. The PCB 206 includes a perforated geometry to facilitate the flow of the epoxy resin. A suitable epoxy resin that is transmissive to IR light is used to prevent occlusion of the ToF sensors 204. For aesthetic purposes, the part 218 could be painted/spray-coated/polished to hide the presence of any sensors 202, 204, 208 incorporated inside. A suitable paint or coating that is transmissive to IR light is used to prevent occlusion of the ToF sensors 204.

The connector 210 relays signals from the sensors 202, 204, 208 to a servo driver/controller PCB. Generally, the connector 210 is attached to the driver/controller PCB of the adjacent or closest servo actuator on the robot which is configured to move the part or surface the proximity sensing skin 200 is laminated to. The connector 210 is routed through the interior of the robot to the servo controller PCB.

The measurements by the sensors 202, 204, 208 are used to switch different modes of operation of the robot or be input to feedback control algorithms to adjust behaviour of the robot. The measurements are used for collision avoidance, speed control and deceleration of motion near detected objects, and touch recognition. For collision avoidance, the proximity sensors 202, 204 are used to maintain a minimum threshold distance between the part 218 the proximity sensing skin 200 is applied to, and surrounding objects. When an object (i.e. a human, another robot or other object) is detected within the minimum threshold distance of the surface by the proximity sensors 202, 204 the robot will switch to a force/torque compensation mode to prevent collision with the object.

The proximity sensors 202, 204 avoid or ignore self-sensing of the robot on which the sensors 202, 204 are themselves on. Depending on the position of the robot arm, and the placement of different proximity sensing skins 200 on different parts of the robot, the capacitive sensors 202 and ToF sensors 204 on a particular proximity sensing skin 200 are automatically activated and deactivated, or their sensing results are ignored, to prevent self-sensing.

Figure 5B:
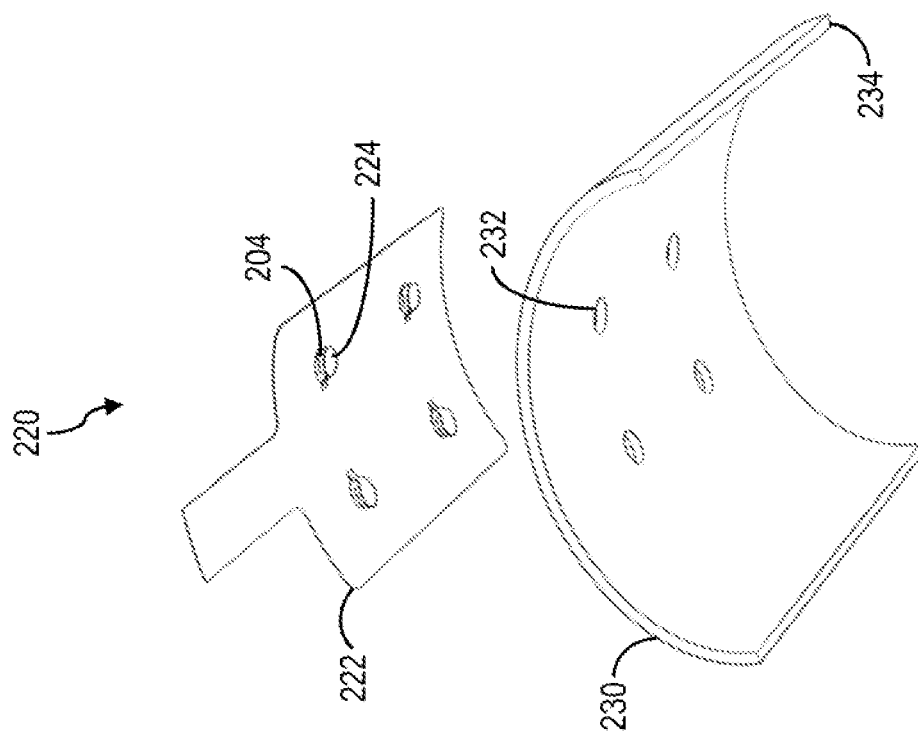
FIGS. 5A-5B are top and bottom perspective views of a proximity sensing skin, according to an embodiment, shown in relation to a robot surface.
Figure 5A:
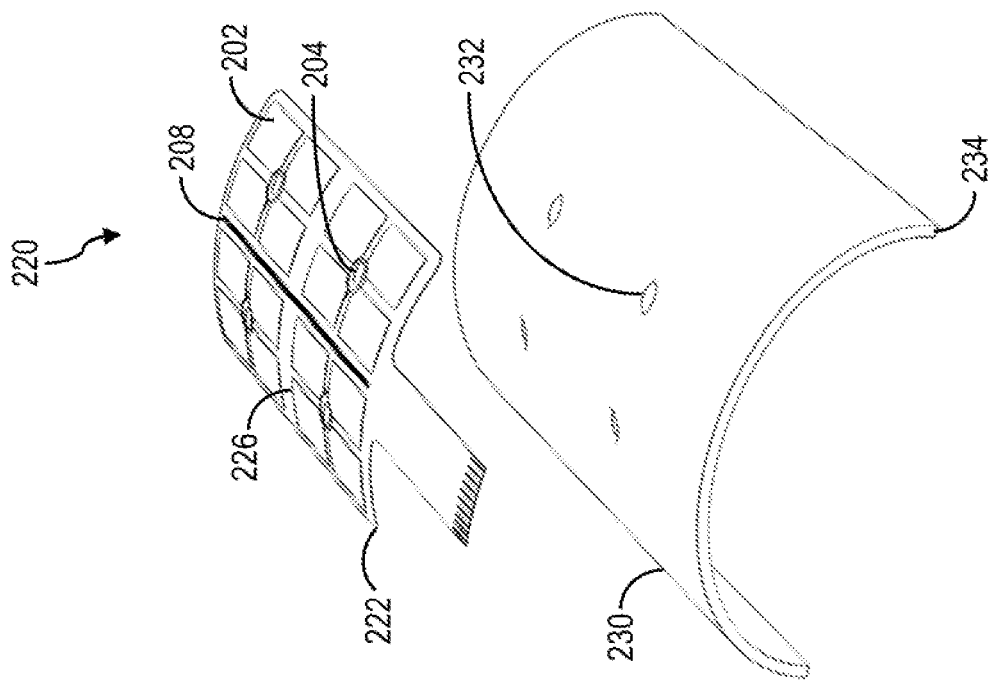

Referring to FIGS. 5A-5B, shown therein is a proximity sensing skin 220, according to an embodiment, shown in relation to a robot surface 230. The proximity sensing skin 220 is substantially similar to the proximity sensing skin 200 in FIG. 4A. The proximity sensing skin 220 includes a copper trace 208, a plurality of capacitive sensors 202 arranged in 2×2 grids on a flexible PCB 222 with a ToF sensor 204 in the center of each 2×2 grid. The PCB 222 includes cutout tabs 224 in the centre of each 2×2 grid on which the ToF sensors 204 are disposed. The cutout tabs 224 are lowered relative to the top surface 226 of the PCB 222 such that the tops of the ToF sensors 204 are substantially in plane with the top surface 226 of the PCB 222.

The proximity sensing skin 220 is applied to a robot surface 230 having apertures 232. When the proximity sensing skin 220 is applied to the robot surface 230, the tabs 224, and the ToF sensors 204 disposed thereon, are received into the apertures 232. This arrangement allows for the robot surface 230 to have a smooth finish and further protects the ToF sensors 204 from damage if the robot surface 230 contacts another object in the region of the ToF sensor 204. The proximity sensing skin 220 may be laminated to the robot surface 230 with epoxy resin to form a monolithic part as described above.

According to some embodiments, infrared (IR) LEDs are incorporated into the flexible PCB 222 to be tracked by VR/AR devices. The pattern of the LEDs on the PCB 222 is unique to each PCB 222 in order to localize the location of the PCB 222 to a part 234 of the robot, for example the base or the end effector, that the proximity sensor skin 222 is applied to. A user wearing a VR/AR headset equipped with an IR camera, can view the IR LED lights to localize the robot relative to the VR/AR headset. This may be done to enable to user to determine where proximity skin is installed on the robot and also determine in what direction(s) the robot is able to sense the proximity of objects.

The IR LEDs are mounted on the tabs 224 of the PCB 222 to prevent any extrusion and texture on the surface 230 of the part 234. If any paint/spray-coating/polishing finish is applied to the part 234 after the proximity sensor skin 222 is applied, the finish is transmissive to IR light so the light emitted by the IR LEDs can pass through. In another embodiment, the IR LEDs are included within the single-point ToF sensors 204 described previously. The brightness of the IR LEDs for AR/VR localization purposes vs. for proximity detection of objects can be adjusted using pulse width modulation in the LED duty cycle.

Referring to FIG. 6A, shown therein is an exploded view of a corrosion inhibiting proximity sensing skin 250 applied to a robot composite part 260a, 260b, according to an embodiment. The composite part 260a, 260b includes a carbon fibre part 260a and a metal bracket 260b that are bonded to form the composite part 260 shown in FIG. 6B. A problem with composite parts is galvanic corrosion. Typically, galvanic corrosion occurs when parts 260a, 260b constructed of different electrically conductive materials are in direct contact leading to preferential corrosion of one of the parts 260a, 260b depending on their electrical conductance.

Galvanic corrosion of the parts 260a, 260b can be mitigated by integrating the corrosion inhibiting proximity sensing skin 250 into the composite part 260. The corrosion inhibiting proximity sensing skin 250 is substantially similar to the proximity sensing skin 220 in FIGS. 5A-5B and includes a plurality of proximity sensors 256. The corrosion inhibiting proximity sensing skin 250 includes a flexible PCB 252 having a folded segment 254 between the sensors 256 and the electrical contacts 258. The proximity sensing skin 250 is applied to the composite part 260a, 260b during bonding of the parts 260a, 206b whereby the folded region 254 interposes the parts 260a, 206b of the bonded composite part 260 as shown in FIG. 6B.

Figure 6C:
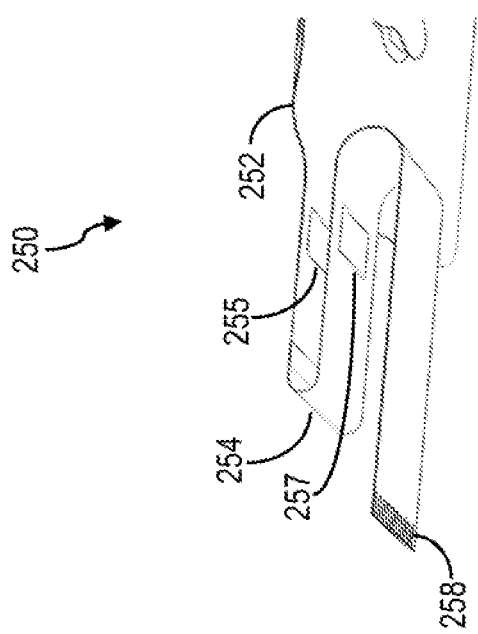
FIG. 6C is a bottom view of the corrosion inhibiting proximity sensing skin shown in FIGS. 6A-6B.

Referring to FIG. 6C, shown therein is a bottom view of the corrosion inhibiting proximity sensing skin 250. The folded segment 254, includes a pair of conductive pads 255, 257 that touch both the metal bracket 260b and the carbon fiber part 260a. A first conductive pad 255 contacts the carbon fiber part 260a and a second conductive pad 257 contacts the metal bracket 260b. A small electric current supplied via the electrical contacts 258 flows between the pads 255, 257 which provides cathodic protection to prevent galvanic corrosion of the parts 260a, 260b.

Figure 7:
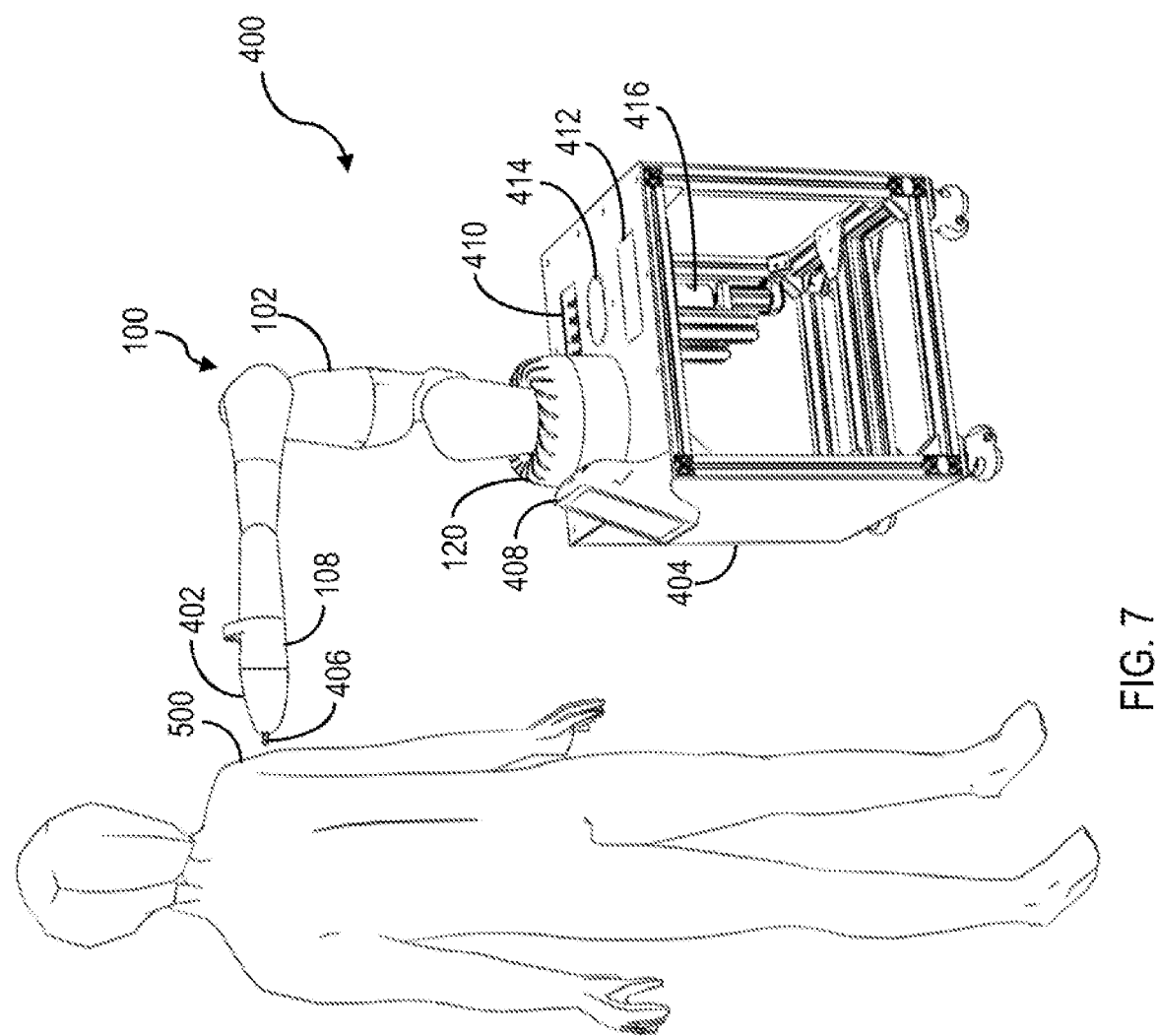
FIG. 7 is a perspective view of an autonomous robotic system, according to an embodiment.

Referring to FIG. 7, shown therein is an autonomous robotic system 400, according to an embodiment. The robotic system 400 is trained to perform autonomous medical procedures and injections. These include but are not limited to subcutaneous injections, intramuscular injections, intra-articular injections, epidural injections, intradural injections, biopsy sampling, fluid aspiration, intravenous access (central-line, peripheral-line and/or peripherally inserted central-line), intra-arterial access (arterial-line), endothelial catheterization, epithelial catheterization and Kirschner wire (K-wire) insertion. In one or more of these applications, either a needle-based or a needle-less-based mechanism could be used to complete the required task, such as drug administration.

The autonomous system 400 includes the autonomous robot apparatus 100 shown in FIGS. 1A-1B with a tool 402 attached to the end effector 108. As described above, the end effector 108 forms electrical and hydraulic/pneumatic connections with the tool 402 upon attachment, to power and control the tool 402. The tool 402 includes a replaceable tip 406 configured for needle-based blood draws and injections or needle-less injections. The tip 406 may include a syringe for blood draws or a vial or cartridge filled with an injectable fluid. The tool 402 further includes sensors to aid in injections and blood draws as described below.

The tool 402 may further include a deformable stretching mechanism (not shown) comprising rigid or flexible linkages which expand radially as the vertical height shrinks. The stretching mechanism is deployed outward during the injection process to stretch the skin of the patient for optimal conditions for injection. This may be appropriate where the patient has a non-ideal skin condition such as wrinkles or lesions. The stretching mechanism will progressively stretch the skin as the end effector 108 of the robot 100 pushes toward the patient's arm (or other body parts). The radial and axial load on the stretching mechanism can be measured by integrating load cell/strain-gauges into the mechanism. It is important to note that the loads/forces acting on the stretching mechanism is not the same as the loads/forces acting on the tip 406 (injecting mechanism).

For sanitary reasons, since the stretching mechanism comes into contact with the patients' bodies, the cover/tips will be replaceable. In another embodiment, the stretching mechanism could be both disposable or non-disposable. The non-disposable design could be made from more permanent materials such as metals (aluminum, stainless steel) or more durable plastics. In this embodiment, the stretching mechanism will have to be sanitized between uses.

The stretching mechanism may be fabricated from soft and/or hard plastics, fabrics, and smart materials (i.e., electro-active polymers, shape memory alloy, or polymer). The stretching mechanism may be integrated with disposable vials to be a single part.

The base 120 of the robot 100 is attached to a support structure 404. The support structure 404 includes a touchscreen display 408 for presenting instructions to the user 500 and receiving input from the user 500 to aid in the robot's 100 interactions with the user 500. For example, the display 408 may present instructions for the user 500 to stand closer to the robot 100 with their arm facing the robot 100 based on sensor measurements from the vision modules detecting the proximity of the user to the robot 100, the end effector 108 or the tool 402. The display 404 may be connected to the robot 100 via the I/O connectors in the base 120 whereby the robot 100 outputs the image for presenting on the display 408.

The support structure 404 includes a plurality of receptacles (or trays) 410, 412. A first receptacle 410 is used for storing empty syringes or cartridges containing an injectable fluid. At least a second receptacle 412 is used for storing waste, such as used cartridges and needles. The receptacles 410, 412 are removable from the support structure 404 to empty or refill the contents. According to other embodiments, the support structure 404 may store a spool or package of vials instead of the receptacle 410.

The robot 100 is configured to autonomously perform injections or blood draws and refill or replace the tip 406 thereafter. One refilling process includes the usage of pre-filled single-use dose vials or multi-dose vials. The single-dose and multi-dose vials may be taken from the receptacle 410 by a reloading mechanism 416. The support structure 404 includes an opening 414 adjacent to the reloading mechanism 416. To replace the tip 406, the robot 100 articulates the arm 102 to drop the old tip 416 into the waste receptacle 412 and then insert the tool 402 through the opening 414. The reloading mechanism 416 then engages the tool 402 to replace the tip 406 with a fresh vial. This refilling method provides a way of re-filling the robot simply and in-frequently by adding fresh vials to the receptacle 410 after a large number of doses have been administered.

Another re-filling process includes using hydraulic pumps connected to a large container of the vaccine/drug (not shown). The fluid is transported to the end effector 108 to refill the tip 406 via the valve array in the base 120 and tubing routed internally through the robot 100. This fluid could be administered to the patient/customer directly using both needle-less or needled methods. Additionally, the fluid could be used to fill an empty vial which then could be used using both needle-less or needled methods.

To articulate the arm 102 for injections and reloading without contacting objects in close proximity such as the user 500 or the support structure 404, the robot 100 views the environment by the vision modules in the base 120 and the end effector 108 as described above. The robot 100 implements AI object detection and is trained to identify objects such as vials, syringes, needles, etc. for specific applications, as well as objects for interaction with, such as the user 500 or the reloading mechanism 416 on the support structure 404. The robot 100 may further include at least one proximity sensing skin laminated to a part of the robot 100, such as the arm 102, the end effector 108 or the tool 402.

As mentioned above, most of the information which is used to determine the location of the injection is obtained by using live vision data (RGB camera, depth vision, IR, Ultrasound, LIDAR, etc.) from the vision module in the base 120. However, during the last moments of contact, the exact location might not be accessible from those sensors because of line-of-sight issues or fast-moving targets. Therefore, a lower resolution but faster (real-time) sensor might be utilized in the vision module of the end effector 108 for fine-tuning and immediate correction of the control system. Additional sensors in the tool 402 or peripheral devices may be connected to the robot 100 to provide additional sensing abilities required for specific applications. These sensors/peripherals and a description of their use are as follows.

Ultrasound- and sonar-based sensors/peripherals are an ideal choice for cheaply detecting internal features of the body such as flesh, bone, and veins/arteries. Sensing these features is crucial for determining the location of the insertion on the patients' body as well as the depth and angle to avoid medical complications and harm to the patient. The 2D & 3D ultrasound data is typically sent to the robot 100 and processed by computer vision algorithms which might include ML/AI such as edge detection, AI-based semantic segmentation, etc.

Infrared vision sensors/peripherals is also another option for detecting anatomical features close to the skin, thus making it useful for the application of intramuscular and intravenous injections and blood draws. Similar to the sonar and ultrasound data, the infrared data is typically processed by computer vision algorithms which might include ML/AI such as edge detection, AI-based semantic segmentation, etc.

Load cells and strain gauge sensors/peripherals are used for measuring the force applied by the robot 100 or the tool 402 when interacting with objects. An important measurement while performing injection/blood draws, whether needle or needle-less, is the applied force/load to the patient and the tool 402 itself. The incorrect application of force could lead to the failure of the operation, harm the patient, cause pain and discomfort, and/or damage the tool 402.

Some medical procedures, as mentioned above, rely on more precise localization of the anatomical features pre-operatively. The localization can be obtained using external markers and imagery obtained by MRI, Radiography, CT scan, or PET scans performed by peripheral devices. The external markers are seen by the vision sensors on the base 120 or the end effector 108 such as the camera or depth sensors; once the external markers have been identified, the medical imagery data can be mapped to the real physical world. Additionally, the 3D data from the depth sensor could be used, either independently or in conjunction with the identified markers, to map medical imagery data as well. Once the medical imagery data is mapped to the physical world, the location of the robot to the relative to the patient and his/her organs are determined.

According to various embodiments, the autonomous robot system 400 is configurable for other applications, interactions and/or collaboration with the humans or other robots or peripheral equipment. The robotic system 400 may be easily adapted by simply replacing the tool 402 with another tool or connecting the robot to peripheral equipment for a specific application as described below.

According to various embodiments, the autonomous robotic system 400 is implemented for needle-based applications. In one embodiment, the needle-based application is intramuscular (IM) or subcutaneous injections such as vaccines. Currently, vaccines are administered to patients by a health care professional resulting in a very labor-intensive process. Using the autonomous robotic system 400 would allow IM injections such as vaccines to be performed autonomously without direct intervention from a healthcare provider.

A comparative analogy can be made to self-checkout lanes at the grocery store in which a store clerk oversees a bay of self-checkout booths. Similarly, with IM injections, a healthcare provider could oversee a bay of autonomous robotic booths that are administering vaccines (or other IM or subcutaneous injections) to patients. In this embodiment, the healthcare professional would only have to intervene if a patient ran into issues with the workflow or if the patient was flagged by the robot 100. This application relies on several of the technological systems disclosed in the present application including, but not limited to, stereoscopic vision, lidar, ultrasound, and collision avoidance.

In another embodiment, the autonomous robotic system 400 is used as a robotic phlebotomist to perform blood draws without direct intervention from a healthcare professional. This embodiment could use additional image guidance like infrared in order to visualize superficial blood vessels. Ultrasound could also be utilized to visualize deeper structures such as blood vessels, muscles, bones, fat, etc. Infrared or ultrasound sensors can be integrated into the tool 402 and/or the vision module in the end effector 108 for this specific application.

In another embodiment, the autonomous robotic system 400 is used for needle-based biopsies. For performing tumor biopsies, the robot 100 could be registered to a preoperative imaging device, such as MRI, to locate a site for the biopsy according to the MRI image and obtain a biopsy sample of the tumor without direct intervention from a healthcare provider.

In another embodiment, the autonomous robotics system 400 is used for spinal blocks or injections such as epidurals and subdural. For example, the robot 100 could administer paralytics to a patient through a spinal block as a part of the pre-operative workflow without direct intervention from an anesthesiologist. In this example, ultrasound would be used for image guidance to improve accuracy. Pre-operative imaging such as MRI could also be integrated in order to further improve the visualization of soft tissue structures like nerve roots.

In another embodiment, the autonomous robotic system 400 is used for intra-articular injections. For example, the robot could use imaging modalities such as ultrasound and or x-ray to visualize the joint space (such as the hip) without direct intervention from a healthcare provider. The robot 100 could then administer an intra-articular injection (such as hyaluronic acid) into the joint space to provide therapeutic relief from osteoarthritis. Other intra-articular injections could include but are not limited to platelet-rich plasma and cortisone.

In another embodiment, the autonomous robotic system 400 is used for hair replacement procedures. In this embodiment, AI could not only be used on the robotics side but also in procedural planning to help the technician assess where to take hair from and where to implant hair. The robot could then harvest and replant the hair without direct intervention from a healthcare professional based on this procedural plan.

In another embodiment, the autonomous robotic system 400 is used for swab testing. This includes but is not limited to nasopharyngeal swabs, oropharyngeal swabs, cervical swabs, urethral swabs, etc. In the example of covid swabs, the robot could administer a swab without direct intervention from a healthcare provider, keeping them safe from the viral spread. This embodiment may use vision technology such as lidar, stereovision and pre-procedural MRI or CT to aid in the positioning of the swab through the robot.

In another embodiment, the autonomous robotic system 400 is used for needle-less injections. In the needle-less method of injecting, the drug/substance is injected without using needles as the name suggests. The injection mechanism simply uses pneumatic pressure as a means of propelling the drug in a jet-like manner inside the patient's tissue. The pneumatic pressure could be generated from a traditional continuously operating compressor or by a local positive-pressure piston in the tool 402 which creates discrete pressure using a spring-loaded latch mechanism.

If a traditional compressor-based pneumatic system is used, the pressure to the tool 402 is controlled and applied using actively controlled pressure regulator valves and flow control valves/solenoids on the valve array in the base 120 of the robot 100. The pressure target of the pressure regulator valve can be electronically controlled from the main robotic control system. It is crucial for the procedure to be controlled precisely since some drugs/vaccines (depending on their molecular structure) are sensitive to this applied pressure, thus, causing them to be adversely affected if the incorrect pressure is applied.

If a spring-loaded latch-like mechanism is used, the automation of the loading of the latch as well as release of the latch could be accomplished using shape memory alloy or electromagnetic actuators in the tool 402. Force and proximity sensors on the end effector 108 could be used to determine the state of the mechanism (i.e., latched, filled, released, etc.) and/or the multi-directional forces acting on the mechanism during different stages of the process (i.e., filling, injection, disposed of, etc.) as described above.

Figure 8B:
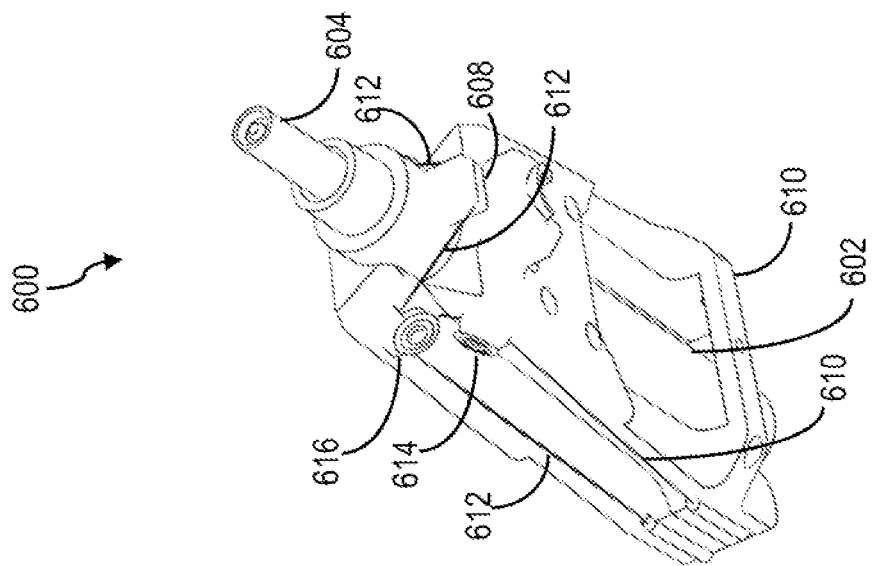
FIGS. 8A-8B are top and bottom perspective views of a tool for needle-less injection, according to an embodiment.
Figure 8A:
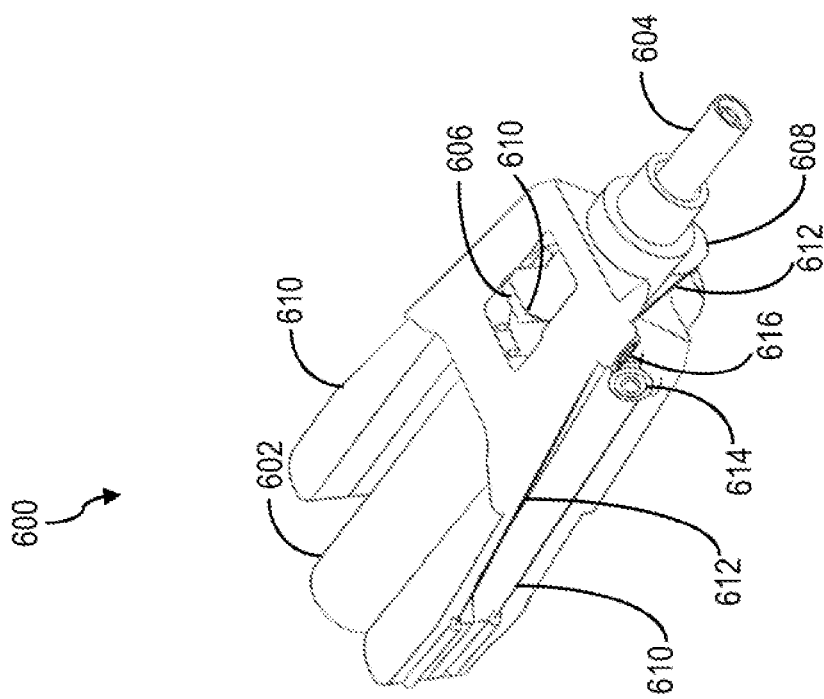

Referring to FIGS. 8A-8B, shown therein, is a tool 600 for needle-less injection, according to an embodiment. The tool 600 may be the tool 402 shown in FIG. 7.

The tool 600 includes a positive-pressure piston injector 602 which creates a discrete pressure to inject the contents of a replaceable vial 604 into a patient. The piston injector 602 includes a first spring-loaded latch 606 to inject the contents of the vial 604 and a second spring-loaded latch 608 to eject the vial 604 from the tool 600 after use. The piston injector 602 may be an off-self component (for example, a Pharma Jet injector) for manual handheld operations.

The piston injector 602 is incorporated into the tool 600 for autonomous injections by the robot. The tool 600 includes a housing 610 for holding the piston injector 602. The housing 610 includes two shape memory alloy actuator wires 610, 612, fixed at both ends and routed over pulleys to engage the spring-loaded latches 606, 608. A first actuator wire 610 is routed over a first pulley system 614 and engages the first spring-loaded latch 606; the second actuator wire 612 is routed over a second pulley system 616 and engages the second spring-loaded latch 608.

The shape memory alloy wires 610, 612 contract and shorten upon heating. The tool 600 includes a heating element (not shown) to alternatively heat the actuator wires 610, 612, causing the wires to constrict thereby depressing the spring-loaded latches 606, 608 to inject the contents of the vial 604, or eject the vial 604 after use.

In the above-described applications for the autonomous robotic system 400, if for any reason non-disposable devices and mechanisms are used, it is crucial that they are thoroughly sanitized between uses. In another embodiment, the autonomous robotic system 400 is used for self-sanitization and/or sanitization of the surrounding environment. A sanitation tool may be attached to the end effector 108 or the robot 100 may be sanitized by an adjacent robot having the sanitizing tool. The sanitizing tool is configured to employ a sanitation method, not limited to: IR or Joules heating; chemical sanitation using alcohol, soap, cleaners, biocides; or pneumatic/mechanical sanitation using compressed air, pressurized water or an abrasive fluid.

According to an embodiment, the end effector 108 includes a high-intensity UV lamp or LED which is used by the robot 100 to self-sanitize itself, the surrounding environment and/or adjacent robots. Additionally, the robot 100 itself could be painted with anti-bacterial IR-transmissive paint to enhance the protection and sanitation in conjunction with the other methods mentioned above.

While the above description provides examples of one or more apparatus, methods, or systems, it will be appreciated that other apparatus, methods, or systems may be within the scope of the claims as interpreted by one of skill in the art.

The invention claimed is:

1. A proximity sensing skin comprising:
    a flexible conductive material for laminating to a surface, the conductive material having a plurality of sensors arranged thereon, the plurality of sensors comprising:
        at least one capacitive sensor, for sensing the proximity of objects up to ~10 centimetres from the surface;
        a single point time of flight sensor, for sensing the proximity of objects from ~10 centimetres up to ~2 metres from the surface, the time of flight sensor comprising:
            a phototransistor; and
            an infrared LED;
        a copper trace for measuring mechanical strain/stress force on the surface to which the proximity sensing skin is laminated; and
    wherein the flexible conductive material relays signals from the plurality of sensors to a servo controller configured to move the surface in response to the signals from the plurality of sensors.

2. The proximity sensing skin of claim 1, wherein the proximity sensing skin is laminated to the surface by epoxy resin forming a monolithic part.

3. The proximity sensing skin of claim 1, wherein the surface is on a composite part, the composite part being constructed of a metal and one of carbon fibre or fibreglass.

4. The proximity sensing skin of claim 3 further comprising:
    a first conductive pad in contact with a carbon fibre segment of the composite part; and
    a second conductive pad in contact with a metal segment of the composite part;
    wherein a current passes between the first and second conductive pad to inhibit galvanic corrosion of the composite part.

5. An autonomous robot apparatus, comprising:
    an articulated robotic arm, comprising:
        a plurality of limb segments connected by hollow joints, wherein the limb segments are rotatable about the joints to move the robotic arm in three dimensions; and
        an end effector removably attached to a terminal limb segment, the end effector comprising:
            a mounting interface for removably attaching a tool, the mounting interface comprising:
                a latch mechanism for locking the tool to the mounting interface;
                a first vision module for measuring the attachment or detachment of the tool at the mounting interface; and
        a base attached to the robotic arm, the base comprising:
            a second vision module for detecting objects in proximity to the robotic apparatus, the second vision module comprising:
                a pair of RGB cameras for stereoscopic depth perception of objects in an environment around the robot apparatus;
                a far-infrared thermal camera for measuring temperature of the objects; and
                a single point time of flight (ToF) depth sensor for measuring distances to the objects;
            a three-axis gimbal configured to point the second vision module to capture a 360-degree view of the environment around the robot apparatus;
        wherein the robot is configured to autonomously articulate the robotic arm to perform one or more trained tasks using the tool while avoiding collisions with the objects detected by the second vision system.

6. The autonomous robot apparatus of claim 5, wherein an emissivity calibration for an object viewed by the thermal camera is calculated and adjusted in real-time, based on the distance of the object measured by the ToF sensor and detection of the object by the RGB cameras.

7. The autonomous robot apparatus of claim 5, wherein the base further comprises a valve array comprising:
    a plurality of solenoid valves in fluidic connection for regulating fluid supply from at least five input lines to a pair of output lines connected to the end effector, whereby a hydraulic/pneumatic fluid is supplied to the end effector via one of the output lines for hydraulic/pneumatic control of the tool.

8. The autonomous robot apparatus of claim 7, wherein the base further comprises:
    a central hollow through which the least five input lines, the pair of output lines and all wiring to the first vision module and the second vision module are routed.

9. The autonomous robot apparatus of claim 8, wherein the pair of output lines and the wiring to the first vision module is routed from the central hollow internally through the plurality of limb segments and hollow joints to the end effector.

10. The autonomous robot apparatus of claim 7, wherein the mounting interface further comprises:
    at least one hydraulic/pneumatic connector for hydraulic/pneumatic control of the tool, wherein the hydraulic/pneumatic connector is in fluidic connection with the pair of output lines.

11. The autonomous robot apparatus of claim 5 further comprising:
    at least one servo motor within each limb segment, for articulating the limb segment, wherein the servo motor is configured to implement a current feedback mechanism for sensing mechanical resistance experienced by the servo motor when moving the limb segment.

12. The autonomous robot apparatus of claim 11 further comprising:
    at least one proximity sensing skin laminated to at least one part of the robot apparatus, the proximity sensing skin comprising:
        a plurality of sensors, comprising:

at least one capacitive sensor, for sensing the proximity of objects up to ~10 centimetres from the surface;

a single point time of flight sensor, for sensing the proximity of objects from ~10 centimetres up to ~2 metres from the surface, the time of flight sensor comprising:
  a phototransistor; and
  an infrared LED;

a copper trace for measuring mechanical strain/stress force on the surface; and a connector for relaying signals from the plurality of sensors;

wherein the connector is connected to a servo motor controller configured to move the part.

13. The autonomous robot apparatus of claim 12, wherein the proximity sensing skin further comprises:
  a plurality of infrared LEDs arranged in a unique pattern on the proximity sensing skin, the unique pattern being visible to an infrared camera on a VR/AR headset connected to the robot apparatus for viewing the unique pattern, wherein the VR/AR headset is worn by a user to localise the robot apparatus relative to the VR/AR headset.

14. The autonomous robot apparatus of claim 13, the infrared LED of the time of flight sensor is visible to the infrared camera on the VR/AR headset connected to localise the robot apparatus relative to the VR/AR headset.

15. The autonomous robot apparatus of claim 13, wherein the base further comprises:
  a plurality of I/O connectors for connecting the robot apparatus to one or more peripheral devices, wherein the peripheral devices include at least the VR/AR headset.

16. The autonomous robot apparatus of claim 13, wherein the 3D orientation of the VR/AR headset, as oriented by the user, is transferred to the gimbal to point the second vision module in real-time.

17. An autonomous robotic system using the autonomous robot apparatus of claim 5 for administering injections, the system comprising:
  a support structure for mounting the base of the autonomous robot apparatus, the support structure comprising:
    a first receptacle for storing disposable cartridges filled with a fluid to be injected into a patient;
    at least a second receptacle for storing waste; and
    a reloading mechanism for loading a disposable cartridge into a tip of the tool attached to the end effector of the robot apparatus;
  wherein the autonomous robot apparatus is configured to:
    move the tool adjacent to the reloading mechanism when the tip is unloaded; and
    move the tool above the second receptacle to dispose of the disposable cartridge after injection;
  while avoiding collisions with the objects detected by the second vision system.

18. The autonomous robotic system of claim 17, wherein the tool further comprises:
  a positive pressure piston injector for injecting the fluid in the disposable cartridge into the patient;
  a first spring loaded latch for releasing the pressure piston to inject the fluid;
  a first shape memory alloy actuator wire routed over a first pulley system to engage the first spring loaded latch;
  a second spring loaded latch for ejecting the disposable cartridge from the tip;
  a second shape memory alloy actuator wire routed over a second pulley system to engage the second spring loaded latch;
  a heating element for alternatively heating the actuator wires; and
  a nozzle for spraying a disinfecting liquid onto the patient in a region to be injected;
  wherein upon heating, the actuator wires contract, depressing the spring loaded latches.

19. The autonomous robotic system of claim 17, wherein the end effector further comprises a high-intensity UV light source for self-sanitization of the autonomous robotic system, wherein the UV light source is activated upon detachment of the tool from the end effector.

20. The autonomous robotic system of claim 17 wherein the support structure further comprises:
  a touchscreen display connected to the robot apparatus, for displaying instructions to the patient to position themselves relative to robot apparatus or the tool;
  wherein the instructions are generated based on the proximity of the patient to the tool as detected by the first vision module or the second vision module.

* * * * *